(12) United States Patent
Vidal

(10) Patent No.: US 6,302,186 B1
(45) Date of Patent: Oct. 16, 2001

(54) PLUNGER FOR A PRESSING FURNACE

(75) Inventor: Patricia E. Vidal, Hillside, NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/431,659

(22) Filed: Nov. 1, 1999

(51) Int. Cl.⁷ ..................................................... B22D 13/00
(52) U.S. Cl. .......................... 164/113; 164/312; 164/516; 164/517; 164/518; 164/519; 264/16; 264/17
(58) Field of Search ..................................... 164/113, 312, 164/516, 517, 518, 519; 264/16, 17

(56) References Cited

U.S. PATENT DOCUMENTS

| | | | |
|---|---|---|---|
| 3,924,031 | * 12/1975 | Nicholas et al. | 427/217 |
| 5,284,808 | * 2/1994 | Damiano et al. | 501/103 |
| 5,833,464 | 11/1998 | Foser . | |
| 5,897,885 | 4/1999 | Petticrew . | |

FOREIGN PATENT DOCUMENTS

| | | |
|---|---|---|
| 0 231 773 | 1/1987 | (EP) . |
| WO 97/01408 | 1/1997 | (WO) . |

* cited by examiner

Primary Examiner—H. Alexandra Elve
(74) Attorney, Agent, or Firm—Ann M. Knab

(57) ABSTRACT

A disposable plunger for use in a pressing furnace for the fabrication of dental restorations. The plunger is fabricated of a refractory investment material such as gypsum-bonded, phosphate-bonded or ethyl silicate-bonded investment materials. The plunger is fabricated by known casting methods. The mold used for making the plunger can be supplied by a manufacturer of molds or can be easily made by using an alumina or similar plunger as a model. Laborious cleaning and grinding are not required with plungers herein described. Cracking problems that occur with prior art plungers are decreased, if not completely eliminated.

5 Claims, 1 Drawing Sheet

PLUNGER FOR A PRESSING FURNACE

FIELD OF THE INVENTION

The present invention relates generally to a process of heat pressing of dental restorations and more specifically to a plunger for use in a pressing furnace for transferring pressure from a furnace piston into an investment ring.

BACKGROUND OF THE INVENTION

Dental materials include porcelain facings, veneers, bridges, inlays, crowns, and a multitude of other products. The first step of the casting of, for example, an inlay or a crown, is the preparation of a wax pattern. The cavity is prepared in the tooth and the pattern is carved, either directly in the tooth or on a die that is a reproduction of the tooth and the prepared cavity. If the pattern is made in the tooth itself, it is said to be prepared by the direct technique. If it is prepared on a die, the procedure is called the indirect technique. However the pattern is prepared, it should be an accurate reproduction of the missing tooth structure. The wax pattern forms the outline of the mold into which the alloy or ceramic is cast. Consequently, the casting can be no more accurate than the wax pattern, regardless of the care observed in subsequent procedures. Therefore, the pattern should be well adapted to the prepared cavity, properly carved, and the distortion minimized. After the pattern is removed from the cavity, it is surrounded by a material which forms an investment. This process is called investing the pattern.

Commonly used investment materials include gypsum, phosphate and silica-based materials. Preferably, silica-based investments fabricated from all or a high percentage of quartz or cristobalite are used as dental investment materials. After the investment material has hardened, the wax is eliminated, typically by heat to provide a mold cavity for forming the dental restoration. The investment includes a pouring channel which is formed by a sprue on the wax model. This provides a channel through which the dental materials are supplied to the mold cavity. Dental materials, such as dental ceramics, may be inserted into a premolding space in the form of an unfinished piece or blank. The blank is softened by heat so that it can be introduced into the molding cavity in a viscous state using fairly low pressure to assume the shape of the mold cavity to form the desired dental prosthesis. This process is called heat pressing and is described in "Hot-Compressed Porcelain Process For Ceramo-Metal Restorations" by E. R. McPhee in *Dental Porcelain: The State of the Art*—1977, edited by Henry Yamada, USC School of Dentistry, Los Angeles, Calif. More recently, the process was described in an article by M. J. Cattel et al., entitled "The Biaxial Flexural Strength of Two Pressable Ceramic Systems" in Journal of Dentistry 27 (1999) 183–196.

A pressing furnace is used to press the ceramic material into the mold cavity and conform the material to the shape of the cavity. The pressing furnace includes a driving plunger (herein referred to as the "internal plunger") that contacts a second or external plunger inserted into a cylindrical mold made from refractory investment. This cylindrical mold is known as an investment ring in the dental field. The external plunger is in contact with the ceramic material. The external plunger transmits the pressing force from the driving plunger to the ceramic material and forces the material through the channel to the cavity. After the pressing operation, the internal plunger is raised, the investment ring and the external plunger are removed from the pressing furnace, and the resultant dental material is removed from the mold. The external plunger must be cleaned after the pressing operation.

In current practice, alumina plungers are used as external plungers. The alumina plungers are intended to be reused and are relatively expensive. Since the external plunger is in direct contact with the ceramic material, it may react or adhere to the ceramic material. Consequently, cracks may form, originating at the interface between the plunger and the porcelain button, and propagating through the pressed shape. One reason for this is the variation in shrinkage and cooling rates between the plunger and the ceramic materials used to form the dental restoration. Moreover, if the ceramic materials stick to the plunger, cleaning becomes difficult, rendering reuse inconvenient and problematic. Removal of the glass-ceramic from the plunger requires grinding, sandblasting, and/or soaking the plunger in acid resulting in usage of time and labor which could otherwise be spent on other more constructive tasks. Furthermore, this cleaning process can weaken and distort the plunger reducing the useful life of the plunger. Other techniques have been attempted to solve plunger-related problems, such as modification of the pressing cycle or usage of a massive metal block as a heat sink to promote fast cooling of the ring in an effort to avoid cracking. Nevertheless, these solutions have not been proven to be fully effective and cracking may still occur from time to time.

There is a need to reduce or eliminate time involved in cleaning the external plunger after completion of the pressing operation. It is desirable that cracking problems occurring during the pressing operation be reduced or eliminated.

SUMMARY OF THE INVENTION

These and other objects and advantages are accomplished by the invention comprising a disposable external plunger for a pressing furnace. The plunger is fabricated of a refractory investment material such as gypsum and phosphate-bonded investment materials comprising silica materials such as quartz or cristobalite or a combination thereof. The plunger is fabricated by known casting methods. The mold used for making the plunger can be supplied by a manufacturer of molds or can be easily made by using an alumina or similar plunger as a model.

The plunger herein provides an efficient and effective way to alleviate problems associated with prior art plungers. It is inexpensive and simple to manufacture and therefore can be disposed of after use. Laborious cleaning and grinding are not required with plungers herein described. Cracking problems that occur with prior art plungers are decreased, if not completely eliminated.

BRIEF DESCRIPTION OF THE DRAWINGS

Features of the present invention are disclosed in the accompanying drawing, wherein.

DESCRIPTION OF THE INVENTION

Figure 1:
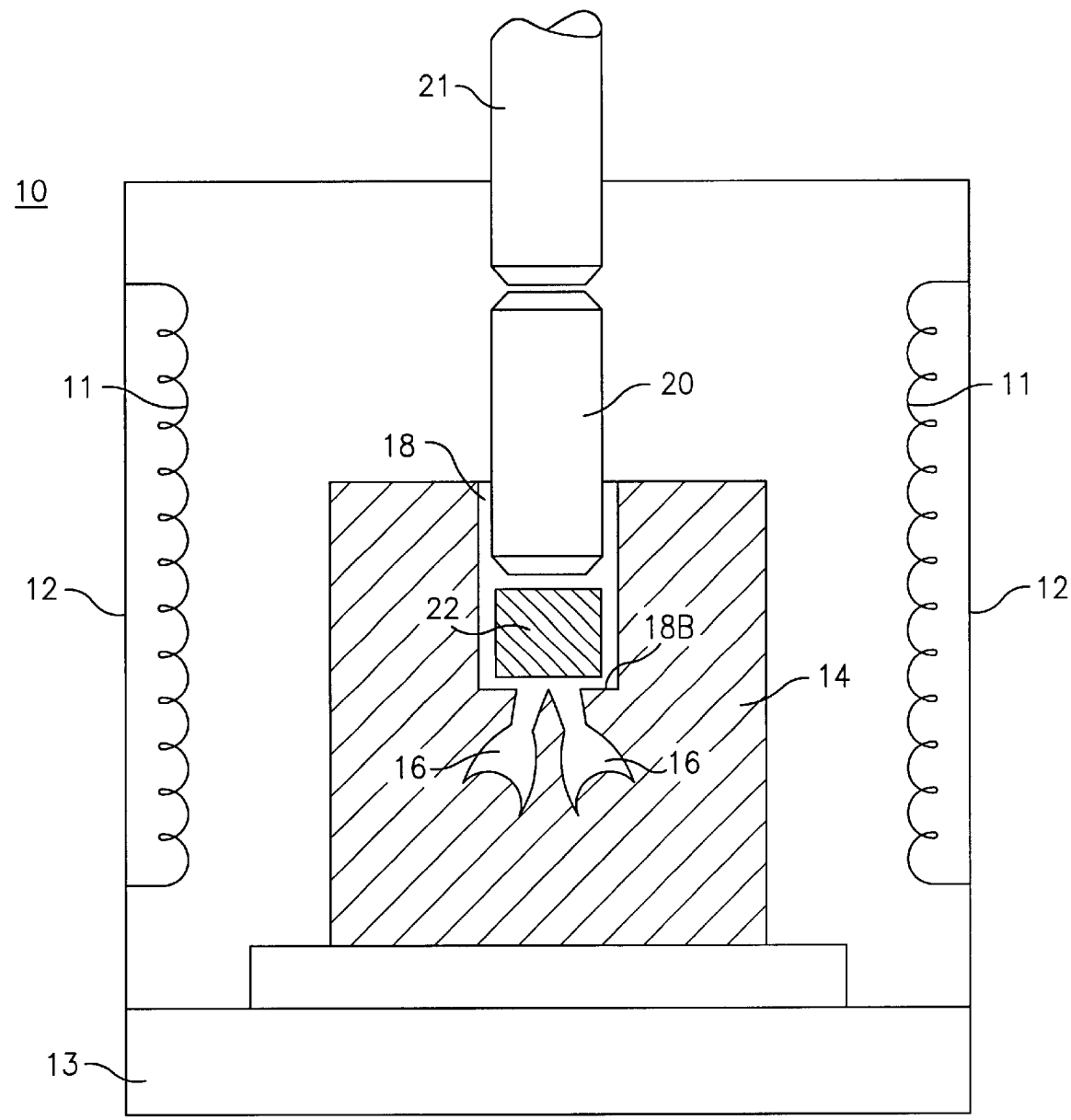
FIG. 1 shows a partial elevational view of a pressing furnace showing a plunger of the invention in pressing position.

As will be appreciated, the invention provides a plunger for use as an external plunger in a pressing furnace used in the manufacture of dental restorations. FIG. 1 is a partial view of a pressing furnace 10 having heating coils 11 disposed proximate walls 12. A pressing or firing platform 13 for holding an investment ring 14 is located at the bottom of furnace 10. Investment ring is an industry term for a cylindrical mold made from a refractory investment material. Investment ring 14 is formed by known methods around a wax pattern. The wax pattern is then eliminated by heat to provide mold cavity 16. A premolding space 18 is also formed in investment ring 14. An external plunger or piston rod 20 is located in premolding space 18. An internal piston or plunger 21 is positioned above external plunger 20 in furnace 10. During the pressing operation, plunger 20 is pushed down to the bottom wall 18B of premolding space 18 by plunger 21. As plunger 20 is pushed down, a blank or pellet 22 is forced into mold cavity 16. The blank is made of a ceramic, metal, alloy, plastic, composite or mixture thereof.

Plunger 20 is fabricated of a refractory investment material such as gypsum-bonded, phosphate-bonded or ethyl silicate-bonded investment materials. These investment materials normally contain up to 80% of a refractory filler such as quartz, cristobolite, other forms of silica, leucite or mixtures thereof. These investment materials are commercially available and are widely used in dental laboratories for various purposes. Other castable refractory materials can be used as well, for example, high temperature melting and casting materials such Ceramacast™ brand castable refractory material from Aremco Products Inc. (Ossining, N.Y.). Ceramcast castables are based on alumina, zirconia, magnesia, zircon, aluminosilicate, cordierite, mica, and mixtures thereof.

Plunger 20 is fabricated by known casting methods such as for example, by casting investment material in a rubber mold. Plunger 20 is strong enough after the burn-out procedure to withstand pressing at temperatures from about 900° C. to about 1200° C. and pressures of up to 7 atm. Normally, pressure of about 5–6 atm is sufficient to cause viscous flow of heated glass-ceramic into the cavity of the mold. The mold used for making plunger 20 can be supplied by a manufacturer of molds or can be easily made by using an alumina or similar plunger as a model. Ten plungers can be cast from one 100 gram bag of investment.

Plunger 20 is easily fabricated of investment material and provides an efficient and effective way to alleviate problems associated with prior art plungers. It is inexpensive and simple to manufacture and therefore can be disposed of after use. Laborious cleaning and grinding are not required with plungers herein described. Cracking problems that occur with prior art plungers are decreased, if not completely eliminated.

The following example illustrates the practice of the invention.

EXAMPLE

An external alumina plunger currently used with the AutoPresss® furnace available from Jeneric®/Pentronz® Inc., Wallingford, Conn. was used as a model to fabricate rubber molds. Four different refractory investment materials were used to make disposable plungers: (1) RapidVest® investment available from Jeneric®/Pentron® Inc., Wallingford, Conn.; (2) Accu-Press™ investment available from Talladium Inc., Valencia, Calif.; (3) PC15™ investment available from WhipMix Corporation, Louisville, Ky.; and (4) Speed™ investment available from Ivoclar North America, Amherst, N.Y. The four materials were mixed with a colloidal silica solution and water as recommended by the manufacturer for the making of investment rings. Distilled water can be used instead of the colloidal silica solution.

The investment mixture was poured into molds and the cast plungers were bench-set and burned-out similar to the process used in the manufacture of refractory rings. The disposable plungers were then ready for use. The plungers were used to press OPC® porcelain pellets available from Jeneric®/Pentron® Inc., Wallingford, Conn., at 1175° C. and LACS pellets (new experimental lithium disilicate pressable ceramics) at 910° C. to 920° C. in an AutoPress® furnace. The plungers were removed thereafter and disposed of. No cracks were present in the porcelain button, sprue or coping. The plungers that were in the burnout oven, but were not used to press any pellets, were removed from the burn-out furnace and used at a later time without noticeable deterioration of strength.

As will be appreciated, the present invention provides a fast and efficient method of pressing dental restorations. A disposable plunger reduces and/or eliminates cracking problems associated with prior art plungers. Cleaning and grinding of plungers are eliminated by the disposable plunger herein described.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A plunger for a pressing furnace for the manufacture of crack-free dental restorations, whereby the plunger is fabricated of a refractory investment material, wherein the refractory investment material comprises a material selected from the group consisting of gypsum-bonded materials, phosphate-bonded materials, and ethyl-silicate-bonded materials; and wherein the plunger is disposable after one use.

2. A furnace for the manufacture of crack-fee dental restorations comprising:

an external plunger fabricated of a refractory investment material, wherein the refractory investment material comprises a material selected in the group consisting of gypsum-bonded materials, phosphate-bonded materials and ethyl-silicate-bonded materials; and wherein the plunger is disposable after one use.

3. A method of manufacturing a crack-free dental restoration comprising:

inserting material in a premolding space of a furnace hereby the premolding space is connected to a mold;

deforming the material by heating and pressing it into the mold with a plunger whereby it conforms to the mold to form a dental restoration, and whereby the plunger is fabricated of a refractory investment material wherein the refractory investment material comprises a material selected from the group consisting of gypsum-bonded materials, phosphate-bonded materials, and ethyl-silicate-bonded materials; and wherein the plunger is disposable after one use;

removing the dental restoration from the mold; and removing said disposing of the plunger.

4. The plunger of claim 1 wherein the refractory investment material further comprises a filler selected from the group consisting of quartz, cristobolite, leucite and mixtures thereof.

5. The plunger of claim 1 wherein it can withstand pressing temperatures in the range of about 900° C. to about 1200° C.

* * * * *